United States Patent [19]

Lewis et al.

[11] Patent Number: 4,566,138
[45] Date of Patent: Jan. 28, 1986

[54] PROSTHETIC DEVICE WITH SPACERS

[75] Inventors: Edward L. Lewis, South Bend; Jack E. Parr, North Webster; Mark A. Fox, Leesburg; Robert L. Fuson, Warsaw, all of Ind.

[73] Assignee: Zimmer, Inc., Warsaw, Ind.

[21] Appl. No.: 725,504

[22] Filed: Apr. 24, 1985

Related U.S. Application Data

[63] Continuation of Ser. No. 473,500, Mar. 8, 1983, abandoned.

[51] Int. Cl.$^4$ ............................................. A61F 1/04
[52] U.S. Cl. .................................. 623/22; 128/92 C; 128/92 CA; 623/16; 623/18
[58] Field of Search ...................... 3/1.9, 1.91, 1.911, 3/1.912, 1.913; 128/92 C, 92 CA

[56] References Cited

U.S. PATENT DOCUMENTS

| D. 230,429 | 2/1974 | Davidson | D83/1 E |
|---|---|---|---|
| D. 232,005 | 7/1974 | Farling | D83/1 E |
| 3,528,109 | 9/1970 | Scales | 3/1.912 |
| 3,605,123 | 10/1971 | Hahn | 3/1 |
| 4,238,207 | 12/1980 | Ruschke | 55/159 |
| 4,281,420 | 8/1981 | Raab | 3/1.912 |
| 4,285,071 | 8/1981 | Nelson et al. | 3/1.912 |
| 4,314,381 | 2/1982 | Koeneman | 3/1.912 |
| 4,316,293 | 2/1982 | Bayers | 3/13 |
| 4,336,618 | 6/1982 | Raab | 3/1.913 |
| 4,365,359 | 12/1982 | Raab | 3/1.912 |
| 4,417,571 | 11/1983 | Nelson et al. | 128/92 B |
| 4,479,271 | 10/1984 | Bolesky et al. | 3/1.911 |

FOREIGN PATENT DOCUMENTS

| 0022308 | 1/1981 | European Pat. Off. | |
| 0120595 | 12/1984 | European Pat. Off. | |
| 2080118 | 2/1982 | United Kingdom | 3/1.912 |

OTHER PUBLICATIONS

Biomet Literature—ES-32 Acetabular Cup—Received Copy 1981, (Actual Date of Publication Not Known).
3M Literature—MMS Acetabular Cups— © 1983.
OEC Literature—S-12 Cup with Cement Spacers, No Date Available.
Zimmer Brochure No. 82-037-0000-0051, Zimmer®, Total Hip Systems for Revision Surgery—Various Acetabular Cups— © 1982.
Zimmer Drawing No. 00-8504-765-01/02 Eftekhar Acetabular Standoff—1981.
Zimmer Advertisement—JBJS, Apr. 1983—vol. 65-A, No. 4—DF-80 TM, Total Hip System—Acetabular Cup.
Deloro Surgical Literature—McKee Total Hip Prosthesis—Acetabular Cup—No Date Available.
Zimmer Brochure—No. 81-037-6504-0948, STH TM —2, Total Hip Prosthesis—Acetabular Cup— © 1981.

Primary Examiner—Richard J. Apley
Assistant Examiner—David Isabella
Attorney, Agent, or Firm—Margaret L. Geringer

[57] ABSTRACT

A prosthetic device adapted to be secured to a supporting bone by a thickness of acrylic bone cement. The prosthetic device has an outer surface which includes a plurality of spacers projecting therefrom. The spacers are made of an acrylic material, such as polymethyl methacrylate (PMMA), and are adapted so that when the prosthetic device is positioned against the supporting bone, the spacers provide a uniform space between the bone and prosthetic device, thus uniformly controlling the thickness of cement. The acrylic spacers will repolymerize and bond with the layer of acrylic bone cement. The nature of the bond formed between the new acrylic bone cement and the acrylic spacers should eliminate the stress concentrations at the interface between the spacers and the cement layer, thereby enhancing fixation of the prosthesis.

9 Claims, 9 Drawing Figures

PROSTHETIC DEVICE WITH SPACERS

This application is a continuation of application Ser. No. 473,500, filed Mar. 8, 1983, now abandoned.

BACKGROUND OF THE INVENTION

The present invention generally relates to prosthetic implants, and more particularly to such implants which use projections or spacers to maintain a uniform layer of bone cement between the prosthesis and the bone to which the prosthesis is to be secured.

Prosthetic devices for replacement of damaged or deteriorating portions of bone are well known in the art. Prosthetic devices for replacement of damaged or deteriorating portions of bone are well known in the art. Prosthetic devices are often secured to the bone with a layer of bone cement. In order to provide a more secure fixation of the prosthesis a uniform, even layer of cement is desired over the entire area of fixation of the prosthesis to the bone.

The acetabulum is one area where this even layer of cement is of particular concern. When both parts of the ball and socket hip joint need replacement, the femoral head is generally replaced with a prosthetic ball-shaped member and the acetabulum is generally lined with a socket or cup member adapted for receiving the ball-shaped member. Various types of spacers have been used to prevent the cup from "bottoming out" of the acetabular bone when cement is used to secure the cup. When spacer devices are not used, the surgeon may apply a layer of cement to the acetabular bone and then place the cup in position against the bone cement. In pressing the cup into place in the cement, the surgeon may cause the cement to unevenly distribute. For example, the cement tends to squeeze out around the edges of the cup, often creating a very thin layer of cement at the portion directly behind the center of the back of the cup, while the cement is much thicker around the edges. This creates a weak securing of the prosthesis.

Prior art devices utilizing spacers include:

U.S. Pat. No. 4,285,071 to Nelson, et al, discloses the use of a plurality of separate or self-contained spacers for use with prosthetic devices, such as acetabular cups. These separate spacers provide a means for controlling uniformity and thickness of the cement applied between the prosthetic device and its supporting bone member. Each separate spacer include a standoff body with a pointed wire outwardly extending therefrom. These spacers are individually positioned by inserting the wire into the bone member. The bone cement layer is then applied, and the prosthetic device member is then placed against the outermost surface of each of standoff bodies. The standoff body of the individual spacers may be made out of acrylic bone cement. The surface of the polymerized acrylic bone cement of the standoff body portion repolymerizes with the new acrylic bone cement layer when it is introduced. The nature of the bond formed between the new acrylic cement layer with the standoff body helps to eliminate stress concentrations at the interface. The disadvantage of the separate spacers is that they have to be individually positioned by the surgeon. This is not only time consuming, but allows for error in positioning of the spacers in relation to each other and the prosthetic device which is to be positioned on the spacers. Also, after the repolymerization, the sharp "thumb tack" like pointed wires remain.

U.K. Patent Application No. GB 2 080 118 A to Hardinge discloses an acetabular cup made out of a plastic material. The external surface of the cup includes a plurality of studs made of the same material as the remainder of the cup. The studs may be either integral with the cup or inserted into the cup. The studs act as spacers to facilitate the formation of a layer of bone cement of substantially constant thickness between the cup and the acetabulum. Spacers such as those of Hardinge which are made of plastic do not incorporate themselves into the cement, but instead they may tend to compartmentalize the cement. Also, plastic spacers may tend to create a potential for stress risers in the surrounding bone cement.

Another prior art acetabular cup is the ES-32 cup sold by Biomet. This cup includes a plurality of protruding spacers to facilitate the formation of a uniform thickness of bone cement to eliminate thick and thin sections of bone cement. The spacers are integrally molded with the polyethylene cup. The cup is reinforced with a metal back cap to guard against deformation and potential resultant cement fixation breakdown caused by excessive cold flow. Openings are provided in the metal cap for the spacers to protrude through. As with the spacers of Hardinge, the plastic spacers of the ES-32 do not incorporate themselves into the bone cement, but instead they may tend to compartmentalize the cement, and might even create stress risers in the surrounding cement.

OBJECTS OF THE INVENTION

A principle object of the invention is to provide a prosthetic device which includes a plurality of spacer elements made from an acrylic material, such as polymethyl methacrylate polymer or copolymer which ar pre-secured thereto for controlling the uniformity and thickness of the cement layer between the prosthesis and its supporting bone member. This allows for precise predetermined location of the spacer elements with respect to the cup.

Another object of the invention is to provide an effective means of adhering the acrylic spacers to the outer surface of the prosthetic element.

A further object of the invention is to provide a prosthetic device which incorporates acrylic spacer elements which repolymerize with the bone cement layer between the prosthesis and supporting bond, but that do not have to be individually positioned on the supporting bone.

SUMMARY OF THE INVENTION

The present invention accomplishes all of the above objects of invention. The present invention provides a prosthetic device which includes a plurality of spacers projecting from the outer surface thereof. The outer surface is defined as that surface of the prosthesis which is to be positioned against the supporting bone member. The prosthesis of this invention is adapted to be implanted with a layer of acrylic bone cement between the outer surface of the prosthesis and the corresponding bone supporting member.

The spacer elements projecting from the outer surface of the prosthetic device facilitate the formation of a uniform thickness of bone cement between the prosthesis and supporting bone. The spacers are made of an acrylic material, such as polymethyl methacrylate polymer or copolymer, such as the same basic polymer used in current bone cements or acrylic elements. The spacers are secured to and project from the outer surface of the prosthetic device. Prosthetic components are generally made from biocompatible metal or plastic materials. Often, various plastic components utilize a metal retainer or reinforcing backing on the surface of the component which is to mate with the supporting bone. The present invention secures acrylic spacers to a biocompatible prosthetic device made of a material other than acrylic, such as a metal or plastic material. The acrylic spacers may be mechanically affixed to the outer prosthetic surface, such as by force fitting the acrylic spacers into complementary holes formed in the outer surface, by threading, or snap fitting. A particularly advantageous means of securing the spacers to the outer surface is so sonically weld them to the surface. This creates a secure adherence of the spacers to either a plastic or metal outer surface.

When the prosthetic device is ready to be positioned in place during surgery, the supporting bone member is prepared according to known surgical techniques. A layer of bone cement is applied to the bone surface, and then the prosthesis is manually positioned into place on the layer of bone cement and pushed into position until the spacers are felt to rest against the bone. It is known that the surface of the polymerized acrylic of the spacers repolymerizes when introduced into contact with the new acrylic bone cement. Thus, the nature of the new bond formed between the new acrylic cement and the acrylic of the spacers should eliminate stress concentrations at the interface. This also should eliminate the problem of compartmentalization of the bone cement layer which tends to occur with plastic or metal spacer elements penetrating the cement layer. The preadherence of acrylic spacers to the prosthetic device provides the advantage of acrylic spacers without the time consuming individual placement of the small spacer elements, as occurs with the previously described Nelson, et al device, and without the need for the sharp wire tracks of Nelson, et al.

The present invention will be described with reference to an acetabular cup member, although it is understood that the principles of this invention may be applied to other prosthetic components.

BRIEF DESCRIPTION OF THE DRAWINGS

These features and objects of the invention, as well as others, will become apparent to those skilled in the art, by referring to the accompanying drawings in which.

DETAILED DESCRIPTION OF THE INVENTION

Figure 1:
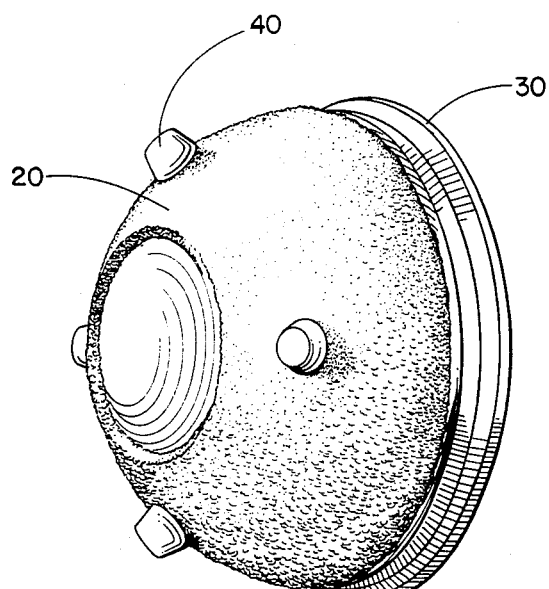
FIG. 1 is a perspective view of an acetabular cup according to the present invention.

Referring now to FIGS. 1-3 and 5 which illustrate a particular embodiment of an acetabular cup prosthesis according to the present invention. The acetabular cup 1 is comprised of an inner articulating surface 10 and an outer surface 20. The cup 1 also includes a sloped surface 35 and a rim 30 between the inner articulating surface 10 and the outer surface 20.

Figure 2:
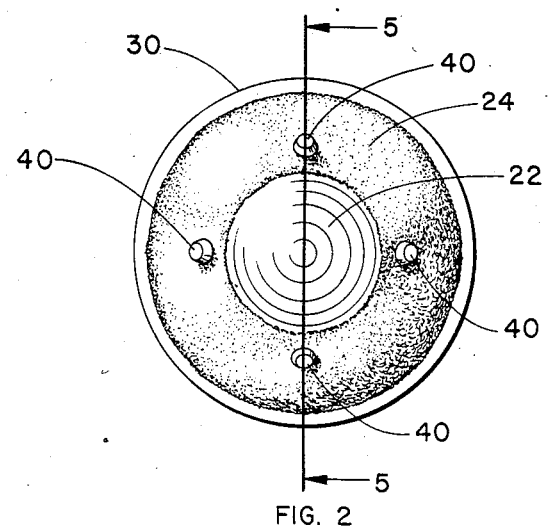
FIG. 2 is a top plan view of an acetabular cup of FIG. 1.
Figure 3:
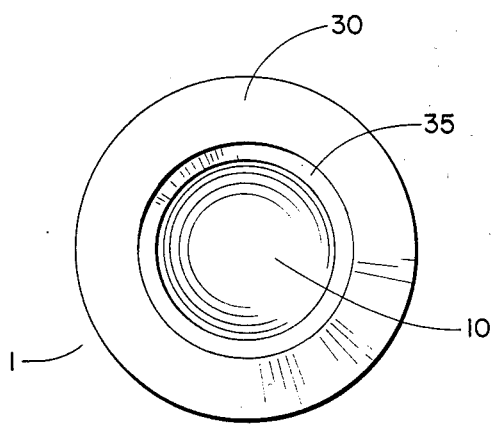
FIG. 3 is a bottom plan view of the acetabular cup of FIG. 1.
Figure 4:
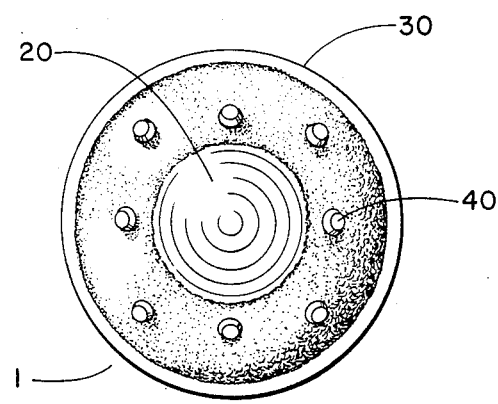
FIG. 4 is a plan view of an alternate embodiment of acetabular cup according to the present invention.

The outer surface 20 includes a plurality of spacer elements 40 which protrude from the outer surface 20. The spacers 40 are generally of uniform thickness and size and are formed in any suitable shape or thickness desired. The protruding portion of the spacers 40 illustrated in FIGS. 1-2 and 4-9 is substantially cylindrical in shape. When the small cylindrical shaped spacers 40 are utilized, it is preferable to use at least three spacers 40 suitably spaced on the outer surface 20 to provide a cup 1 which will be evenly balanced on the supporting acetabular bone member when positioned in place to provide a uniform space between the outer surface 20 and the supporting bone member. Any suitable arrangement of the spacers 40 may be used. FIGS. 1 and 2 illustrate a cup 1 with four spacers 40, while FIG. 4 illustrates a cup 1 with eight spacers 40 spaced uniformly about the outer surface 20.

Figure 5:
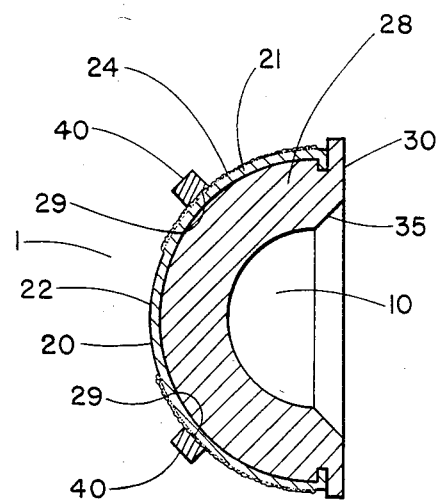
FIG. 5 is a side sectional view taken along lines 5—5 of FIG. 2.

FIG. 5 illustrates an acetabular cup which includes a bearing liner member 28 and a metal shell 21 backing the liner 28. The liner may be made of a plastic bearing material, such as ultra high molecular weight polyethylene material, although other suitable bearing surface materials, such as ceramic, may be used. Various materials may be used for the metal shell 21, such as titanium, cobalt-chrome, high grade stainless steel or a metal/plastic composite. Conventional manufacturing methods may be used for forming the liner member 28 and the metal shell 21.

The outer surface 20 may further include a thin layer of porous metallic beads such as is shown in FIGS. 1, 2, 4, and 5. These Figs. illustrate a nonbeaded portion 22 and a beaded portion 24 on the outer surface 20. Various portions of the outer surface 20 may be covered with such a layer of porous metal beads, or the whole outer surface 20 may be completely covered with the beaded surface. The porous beaded surface may be of the type further described in U.S. Pat. No. 3,605,123 to Hahn, although other means of creating a porous surface may be used. The porous beaded surface enhances the fixation of the bone cement applied during surgery to the outer surface 20 of the cup 1.

The spacers 40 are made from an acrylic material, such as polymethyl methacrylate polymer or copolymer or other comparable material. Various methods of forming the pegs may be used. The spacers may be formed by using a currently available bone cement prepolymer-monomer mix, followed by injecting the mixed material into an appropriate mold or cavity, or the use of an injection mold to form the spacers from the polymethyl methacrylate polymer without the prepolymer-monomer step could be utilized. The methods of forming polymers is well known in the art, and any suitable method could be used to form the desired shape of the spacers. Another alternative is to buy preformed acrylic rods and cut them off to the desired length.

In a particularly advantageous embodiment of the invention shown in FIG. 5, the acrylic spacers 40 are sonically welded to the outer surface 20 of the cup 1 creating a bonding interface 29 between the spacer 40 and the metal outer surface 20. The use of ultrasonic welding for bonding of one polymer to another or for inserting metal inserts into polymers is well-known. The energy is supplied by a machine which generates the ultrasound frequency of approximately 20,000 Hz which is directed through a conveyance mechanism, i.e., the horn, to the parts to be welded or formed. The process can be described as follows: (1) the energy is transmitted through the interface between the horn and the component part; (2) through the solid portion of the part; and (3) concentrated at the interface between the two components to be welded. This concentration of energy is due to a point or line contact between the two component parts. The subsequent energy release, i.e., vibration, proceeds to heat the interface. The temperature rises to a level where the polymer will soften, possibly even melt. This subsequent softening allows the material to become viscoelastic and flow into and around crevices in the metal shell 21 such as into the porous beaded surface 24, as shown in FIG. 5. (In the case of two polymers, such as when the acrylic spacers are being welded to a polyethylene cup which does not have a metal shell, as in FIG. 6, the melts intermingle at the molecular level.) The time of welding is approximately one to two seconds. The pressure is held without vibration to allow the polymer to cool and set up.

The following is a suitable approach used in bonding the acrylic spacers 40 to the porous outer surface of the metal-backed acetabular cup 1, such as that shown in FIGS. 1-2, 4-5. The procedure is as follows: (1) the cup 1 is placed in a fixture; (2) the spacer 40 is held against the porous surface 24 of the cup 1 in the desired position by a fixture; (3) the horn of the ultrasonic machine is put in contact over the broad base area of the spacer 40; (4) with the introduction of the ultrasound energy, the small area of contact 29 between the porous spicules of the metal-backed cup and the acrylic spacer 40 becomes the energy release point; (5) the polymer melts and flows into and around the undercut and porous surface; and (6) upon cessation of the ultrasound energy, but with continued pressure, the polymer in the spacer 40 would then solidify and the spacer would be securely adhered to the porous beaded surface 24 of the metal shell 21.

Other suitable alternate methods for fastening the spacers 40 to the metal shell 21 could be used as follows: (1) the softening of the end of the spacer 40 by solvent immersion and subsequent forcing of this softened spacer into the porous surface 24 of the metal shell 21; (2) melting of the end of the spacer 40 by contact with a hot surface, and with rapid transfer forcing this into the porous surface 24 of the metal shell 21; (3) forming the spacers 40 directly into the cup from a prepolymer monomer mix, such as is used in current bone cement preparations; (4) injection molding the spacers 40 directly onto the metal shell 21 through the use of a mold to hold the acetabular cup 1 during molding; and (5) any combination of the above that would permit the polymer to be intruded into the porous surface 24 of the metal shell 21 and subsequently have a hard, suitably-shaped spacer protrusion. Also, other suitable means of providing a roughened or textured adhering surface of the metal shell 21 other than the porous beaded surface 24 may be used.

Figure 6:
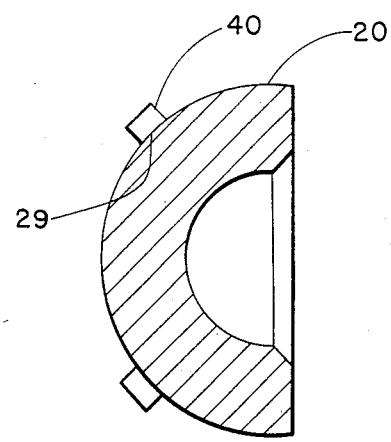
FIG. 6 is a side sectional view of an alternate embodiment of an acetabular cup according to the present invention.

FIG. 6 illustrates an acetabular cup 1 which is formed of a plastic material, such as polyethylene. The cup 1 of FIG. 6 does not include a metal shell. The spacers 40 of FIG. 6 are adhered into position on the outer surface 20 creating a bonding interface 29 between the spacer 40 and the polyethylene outer surface 20. As previously described, sonic welding may be used to affix the acrylic spacers 40 to the outer surface of the plastic outer surface 20. When sonic welding the acrylic spacers 40 to a plastic surface 20, the materials at the bonding interface 29 intermingle at the molecular level to form a secure adherence.

Other means to adhere the acrylic spacers to the outer surface 20 of the cup 1 may also be used, such as various mechanical fixation means.

Figure 7:
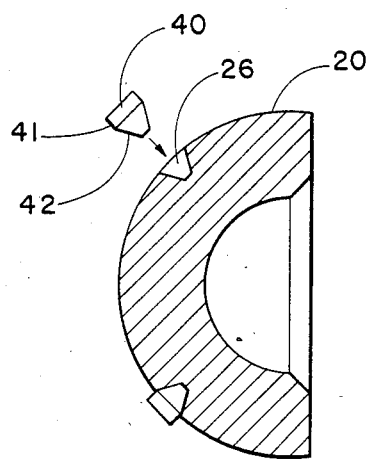
FIG. 7 is a side sectional view of another alternate embodiment of an acetabular cup according to the present invention.

FIG. 7 shows a polyethylene cup which includes holes 26 in the outer surface 20 of the cup 1. The spacers 40 of FIG. 7 include an upper portion 41 which protrudes from the outer surface 20 and a lower surface 42 which is sized to be tightly press fit into hole 26. The lower portion 42 is slightly larger in size than the corresponding hole 26 to create a tight press fit.

Figure 8:
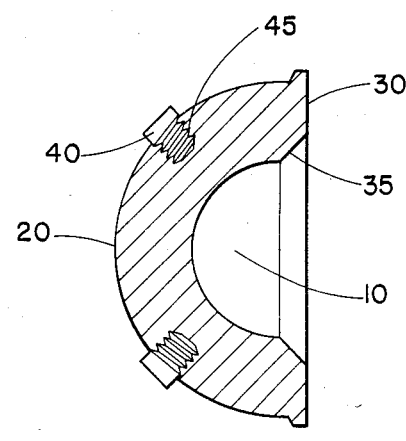
FIG. 8 is a side sectional view of a still further alternate embodiment of an acetabular cup according to the present invention.

FIG. 8 illustrates a similar polyethylene cup 1 except that the holes 26 are threaded and the lower portion 42 of the spacer 40 has been formed with corresponding threads 45 to secure the acrylic spacer 40 into the polyethylene cup 1.

Figure 9:
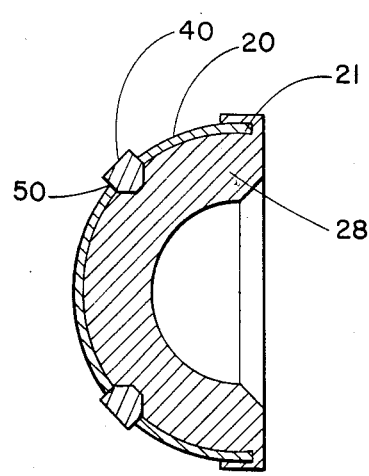
FIG. 9 is a side sectional view of another alternate embodiment of an acetabular cup according to the present invention.

FIG. 9 illustrates a cup 1 with a polyethylene liner 28 and a metal shell 21. The metal shell 21 includes holes 50 through its surface located above a corresponding hole 26 in the polyethylene liner 28. This enables the spacer 40 to be force fit or otherwise mechanically secured through liner 28 such that the acrylic spacer 40 protrudes from the outer surface 20.

Other mechanical means, such as a snap fit of the spacer 40 in through the outer surface 20 of the cup 1, (not shown) may be utilized to affix the acrylic spacer 40 directly to the metal or polyethylene surface of the acetabular cup 1.

The outer surface 20 may also be coated with a thin layer of polymethyl methacrylate (PMMA) film (not shown) which also aids in enhancing the bond between the bone cement applied during surgery and the outer surface 20 of the cup 1. U.S. Pat. Nos. 4,281,420; No. 4,336,618, and No. 4,365,359 to Raab are examples of such thin films of PMMA material being applied to the outer surface of prostheses on the portion adapted to be in contact with the supporting bone. Again, the layer may cover various portions of this contacting surface or all of it, as desired.

The cup 1 of the present invention, which includes acrylic spacers 40 directly adhered to the cup 1, is applied during surgery directly to a layer of new acrylic cement which has been applied to the acetabulum. The cup 1 is manually pushed into position until the spacers 40 are feld to rest against the supporting acetabulum. The polymerized acrylic spacers 40 then repolymerize with the new acrylic cement layer thus forming a new bond. This bond should eliminate stress concentrations at the interface of the spacers 40 which may tend to occur with spacer elements of metal or plastic material. The present invention thus avoids the tedious individual placement of individual acrylic spacer elements and avoids the need for the wire pins of Nelson, et al which remains after polymerization has taken place.

While this invention has been described in terms of various particularly advantageous embodiments, those skilled in the art can appreciate that modifications can be made without departing from the spirit and scope of the invention.

We claim:

1. An acetabular cup to be secured to a supporting bone member by a thickness of acrylic bone cement applied therebetween comprising an inner ultra high molecular weight polyethylene member having a metal outer shell wherein said shell further includes a porous outer surface over at least a portion thereof and said porous surface having a plurality of spacers adhered thereto and projecting a predetermined distance therefrom, said spacers being composed at least in part of acrylic material.

2. The acetabular cup of claim 1, wherein said spacers are composed wholly of acrylic.

3. The acetabular cup of claim 1, wherein said acrylic is polymethyl methacrylate.

4. A method of preparing a metal-backed acetabular cup having a plurality of acrylic spacers on the outer surface thereof comprising the following steps:
    (a) providing a porous surface over at least a portion of the metal outer surface of the cup;
    (b) forming an acrylic material into a suitable shape for spacers; and
    (c) adhering said spacers to said porous surface at predetermined positions, such that the contacting surface of the spacer melts and flows into the porous surface, and then hardens, forming a secure attachment of the spacer to the porous surface of the cup.

5. The method of claim 4, wherein the method of adhering includes the step of sonically welding said spacers to the porous surface.

6. The acetabular cup of claim 1, wherein said spacers are secured to said outer porous surface by means of a sonically welded bond.

7. The acetabular cup of claim 1, wherein said porous surface is a metallic beaded porous surface.

8. The acetabular cup of claim 1 wherein said spacers have substantially the same height and are positioned on the outer surface for providing a uniform space to be filled by bone cement between the acetabular cup and the supporting bone when the cup is positioned against said supporting bone.

9. A method of preparing a metal-backed acetabular cup having acrylic spacers on the outer surface thereof comprising the following steps:
    (a) providing a porous surface over at least a portion of the metal outer surface of the cup;
    (b) placing the cup in a suitable holding fixture;
    (c) forming an acrylic material into a suitable shape for spacers;
    (d) holding a spacer against the porous surface in the desired predetermined position;
    (e) placing the horn of an ultrasonic machine in contact with the broad base area of the spacer;
    (f) introducing the ultrasonic energy;
    (g) melting the contact surface of the spacer, such that the acrylic contact surface melts and flows into the porous surface that the spacer is in contact with;
    (h) solidifying of said acrylic upon cessation of ultrasound energy, providing secure adherence of the spacer to the porous outer surface of the cup; and
    (i) repeating of steps (d) through (h) for each spacer to be adhered.

* * * * *